United States Patent [19]

Kaplan

[11] Patent Number: 4,663,458

[45] Date of Patent: May 5, 1987

[54] WATER SOLUBLE SALT COMPOSITION OF M-AMSA

[75] Inventor: Murray A. Kaplan, Syracuse, N.Y.

[73] Assignee: Bristol-Myers Company, New York, N.Y.

[21] Appl. No.: 807,006

[22] Filed: Dec. 9, 1985

[51] Int. Cl.$^4$ .................. C07D 219/10; A61K 31/47
[52] U.S. Cl. ................................................. 546/106
[58] Field of Search ........................ 546/106; 514/297

[56] References Cited

U.S. PATENT DOCUMENTS 4,399,283  8/1983  Fisher et al. ........................ 546/106

OTHER PUBLICATIONS

The Merck Index, 8th ed., Stecher, ed., Merck & Co., Rahway, N.J., (1968), pp. 848–849.

Primary Examiner—Donald G. Daus
Assistant Examiner—Diana G. Rivers
Attorney, Agent, or Firm—David M. Morse

[57] ABSTRACT

This invention relates to novel compositions of the antitumor agent [4'-9-(acridinylamino) methanesulfon-m-anisidide] (m-AMSA). The m-AMSA lactate salts in combination with Tween-80 provide a highly stable, ready to use aqueous product.

8 Claims, No Drawings

WATER SOLUBLE SALT COMPOSITION OF M-AMSA

BACKGROUND OF THE INVENTION

1. Field of the Invention

The novel compositions of the present invention possess the advantageous pharmacological properties of the known free-base compound and in addition have unexpectedly high water-solubility, thus allowing preparation of useful dosage forms for intravenous administration.

2. Description of the Prior Art

The acridine derivative m-AMSA [4'9-(acridinylamino) methanesulfon-m-anisidide] has been reported by Cain, et al. in Europ. J. Cancer 10:539–549 (1974) to possess significant antitumor activity in animal tumor systems.

When an antitumor agent such as m-AMSA is employed for pharmaceutical use, it is recognized that solubility of the agent is often the controlling factor in determining route of administration and dosage forms. For instance, a water-soluble substance can be generally administered intravenously whereas a water-insoluble material is limited to other forms of parenteral administration such as intramuscular and subcutaneous. A therapeutic agent having water solubility also facilitates preparation of oral and non-intravenous parenteral dosage forms. Thus, it is decidedly advantageous if a therapeutic agent is water-soluble, particularly when one considers that the most direct route for achieving therapeutic blood levels of a drug is by intravenous administration.

The free-base form of m-AMSA has very limited solubility in water and thus cannot be used as a dosage form for intravenous administration. Attempts have been made to prepare acid addition salts to overcome this solubility problem, but the reported monohydrochloride and monomethanesulfonate salts also proved insufficiently water-soluble.

The m-AMSA formulation presently in clinical use consists of two sterile liquids combined just prior to use. A solution of m-AMSA in anhydrous N,N-dimethylacetamide is contained in an ampule. A separate vial contains an aqueous L(+)-lactic acid solution for use as a diluent. When mixed, the resulting m-AMSA solution is administered by i.v. infusion.

While the present clinical formulation provides an intravenous dosage form, it suffers from several disadvantages. In addition to the obvious difficulties in preparing and administering the dosage form, it contains dimethylacetamide as a vehicle. Dimethylacetamide has been reported to show various toxic symptoms in animals and may thus prove to be unacceptable or undesirable as a pharmaceutical vehicle.

It is accordingly an object of the present invention to provide ready to use, stable, aqueous solutions of therapeutically acceptable forms of m-AMSA which can be administered intravenously, as well as by other routes, and which do not contain or require dimethylacetamide as a pharmaceutical vehicle. This object as well as other features and advantages of the invention will be readily apparent to those skilled in the art from the disclosure set out below.

SUMMARY OF THE INVENTION

The present invention provides stable, ready to use aqueous solutions of m-AMSA lactate. The compositions consist of a mixture of m-AMSA lactate salt solutions and polysorbate 80, the ratio of the polysorbate 80 to m-AMSA lactate salts being from about 10:1 to about 20:1. Preferably, it has been found desirable to use about 5 mg/ml of m-AMSA as lactate salts in about 5–10% (V/V) polysorbate 80.

DETAILED DESCRIPTION

Many conventional pharmaceutically acceptable acid addition salts of m-AMSA are only slightly soluble in water and are thus unsuited for preparation of aqueous intravenous solutions. This is evident from literature references to the hydrochloride and methanesulfonate salts.

It has been found that salts of m-AMSA and lactic acid in a molar ratio of 1:1 are soluble at concentrations as high as 5 mg/ml.

It has also been recently found in investigating the aqueous solubility properties of certain m-AMSA lactate salts which are soluble at concentrations as high as 5 mg/ml, that solutions at such concentrations can result in precipitates under extended storage at 24° C.

An investigation of the solubility properties of the crystalline L(+)-monolactate salts of m-AMSA indicates that an m-AMSA L(+)-lactate monohydrate salt crystallized out of aqueous solution posseses an aqueous solubility of about 2.5 mg/ml, with excellent reconstitution rates and the stability necessary for use as an intravenous drug.

The m-AMSA L(+)-lactate monohydrate salts effectively eliminate the solubility problems encountered with lactate salts at concentrations greater than 2.5 mg/ml. While such solubility is adequate for most purposes, it has now been discovered that higher concentrations of a stable solution may be obtained when 5 to 10% (V/V) polysorbate 80 is used in preparation of the 5 mg/ml m-AMSA lactate dosage form.

Polysorbate-80 used in admixture with the salts of the present invention or as a component of the composition of the present invention is a complex mixture of polyoxyethylene ethers of mixed partial oleic esters of sorbitol anhydrides. Polysorbate-80 is marketed by Atlas Chemical Industries, Inc. of Wilmington, Del. under the Tradename "Tween ®-80". It is an emulsifying and dispersing agent used in the preparation of pharmaceuticals.

The m-AMSA/lactic acid composition is prepared by mixing m-AMSA base and L(+) or D(−)-lactic acid in a ratio of 1.0 to 2 moles of lactic acid per mole of m-AMSA in water containing 5–10% (V/V) polysorbate 80.

For preparation of unit dosage forms of the present compositions, the m-AMSA base may be used in any therapeutically effective dose. In the treatment of mammalian tumors, the salts and compositions of the present invention may be administered either orally or parenterally, but preferably in dosages (adjusted for the amount of the m-AMSA base) and according to regimens previously disclosed in the literature. A suggested dosage range of m-AMSA base in a unit dosage form is from about 20 to 100 milligrams.

The aqueous compositions provided by the present invention exhibit substantially the same pharmacological properties as the prior art m-AMSA forms. Because of their water-solubility, these dosage forms can be used for intravenous administration which do not contain an undesirable pharmaceutical vehicle such as dimethylacetamide.

The liquid compositions of the present invention may be used to prepare oral or non-intravenous parenteral dosage forms as well as the preferred intravenous injectable product. The compositions have acceptable stability in aqueous solution and permit administration of an effective dose of m-AMSA in a relatively small volume of parenteral solution.

The compositions of the present invention may be administered either orally or parenterally, but preferable parenterally, in dosages (adjusted for amount of m-AMSA activity) and according to regimens previously disclosed in the literature. A particularly preferred dosage form is a reconstituted aqueous solution having 5 mg/ml of m-AMSA activity.

In the above formulations, a mixture of m-AMSA-L(+)-lactate and 5-10% (V/V) polysorbate-80 will provide a 5 mg/ml m-AMSA solution which will not precipitate.

The m-AMSA-L(+)-lactate aqueous solutions containing 5% to 10% (V/V) polysorbate-80 are stable for at least one year at 20°-25° C. with less than 10% activity loss and unlike m-AMSA lactate salt formulations which contain 1 mole of L(+)-lactic acid in excess, but no polysorbate-80, show no precipitation during such time.

The following examples are given in illustration of, but not in limitation of, the present invention.

EXAMPLE 1

The m-AMSA-L(+)-lactate-polysorbate-80 dosage form of the present invention was prepared by the following procedure:

One gram of m-AMSA base was slurried, at 20°-25° C., in 170 ml of Sterile Water for Injection, U.S.P.

Ten ml. of polysorbate-80 was added to the slurry. Two molar equivalents of L(+)-lactic acid, (0.458 g) were then gradually added, while stirring was continued over 10 minutes to disperse all components. A pH 3.5-4.0 solution or near solution was obtained. The volume was then brought up to 200 ml with Sterile Water for Injection, U.S.P. and stirred for an additional 1 hour. The resulting solution contained 5 mg/ml of m-AMSA activity and 5% (V/V) polysorbate-80.

The solution was passed under a nitrogen atmosphere through a 0.22 micron pore size membrane filter using aseptic technique and the filtrate collected in a suitable sterile container.

The filtrate was then filled under asceptic conditions into suitable vials and sealed.

EXAMPLE 2

Five mg/ml of an m-AMSA-L(+)-lactate/polysorbate-80 solution was prepared according to Example 1. The solution was subjected to accelerated storage with the following results:

| Time | 56° C. | 45° C. | 37° C. | 25° C. |
|---|---|---|---|---|
| | 5% polysorbate-80/% Loss | | | |
| 1 week | 6.0 | +1.8 | — | — |
| 2 weeks | — | 1.8 | — | — |
| 1 month | — | 0 | +1.0 | — |
| 2 months | — | — | +0.5 | — |
| 3 months | — | — | 1.0 | — |
| 6 months | — | — | — | 0.4 |
| 12 months | — | — | — | 2.6 |
| 24 months | — | — | — | 1.8 |
| | 10% polysorbate-80/% Loss | | | |
| 1 week | | 5.2 | | |
| 2 weeks | | 4.0 | | |
| 1 month | | 9.9 | 6.2 | |
| 2 months | | | 3.5 | |
| 12 months | | | | 0 |

Based on the above data it is predicted that the compositions should lose less than 10% activity when stored up to two years at 25° C.

What is claimed is:

1. A ready to use, stable aqueous solution of a lactic acid salt of m-AMSA in combination with polysorbate-80.

2. The composition of claim 1 wherein the acid salt is the L(+)-lactate salt.

3. The composition of claim 1 wherein the acid salt is the D(−)-lactate salt.

4. The composition of claim 1 wherein the acid salt is the D,L-lactate salt.

5. A ready to use, stable, aqueous solution of a lactic acid salt of m-AMSA in combination with polysorbate-80, the ratio of polysorbate-80 to m-AMSA used to prepare the salt being from about 10:1 to 20:1.

6. The composition of claim 5 wherein the acid salt is the L(+)-lactate salt.

7. The composition of claim 5 wherein the acid salt is the D(−)-lactate salt.

8. The composition of claim 5 wherein the acid salt is the D,L-lactate salt.

* * * * *